(12) United States Patent
Tilg et al.

(10) Patent No.: US 6,808,914 B2
(45) Date of Patent: Oct. 26, 2004

(54) PROCESS FOR THE PREPARATION OF L-AMINO ACIDS BY FERMENTATION AND NUCLEOTIDE SEQUENCES CODING FOR THE ACCDA GENE

(75) Inventors: Yvonne Tilg, Wuppertal (DE); Bernhard Eikmanns, Ulm (DE); Lothar Eggeling, Julich (DE); Hermann Sahm, Julich (DE); Bettina Möckel, Bielefeld (DE)

(73) Assignee: Degussa AG, Dusseldorf (DE)

( * ) Notice: Subject to any disclaimer, the term of this patent is extended or adjusted under 35 U.S.C. 154(b) by 270 days.

(21) Appl. No.: 10/024,370

(22) Filed: Dec. 21, 2001

(65) Prior Publication Data

US 2002/0142405 A1 Oct. 3, 2002

Related U.S. Application Data

(62) Division of application No. 09/362,899, filed on Jul. 29, 1999, now Pat. No. 6,361,986.

(30) Foreign Application Priority Data

May 27, 1999 (DE) .......................................... 199 24 365

(51) Int. Cl.[7] .............................. C12N 9/88; C12N 1/20; C12P 13/04; C12P 13/22; C12P 13/06
(52) U.S. Cl. .............................. 435/232; 435/4; 435/6; 435/28; 435/69.1; 435/183; 435/200; 435/252.3; 435/252.32; 435/320.1; 435/41; 435/106; 435/107; 435/108; 435/109; 435/110; 435/113; 435/115; 435/116; 536/23.2; 536/23.5; 536/23.7
(58) Field of Search .......................... 435/4, 6, 28, 41, 435/69.1, 106–116, 183, 200, 232, 252.3, 252.32, 320.1; 536/23.2, 23.5, 23.7

(56) References Cited

FOREIGN PATENT DOCUMENTS

| EP | 197 335 | 10/1986 |
|---|---|---|
| EP | 358 940 | 10/1986 |
| EP | 752 472 | 1/1997 |

OTHER PUBLICATIONS

Eikmanns, Bernhard et al., "Nucleotide sequence, expression and transcriptional analysis of the Corynebacterium glutamicum gltA gene encoding citrate synthase," Microbiology (1994), 140, Nr. 8, pp. 1817–1828, XP–000957470.

Jager, Wolfgang et al., "A Corynebacterium Glutamicum gene encoding a two–domain protein similar to biotin carboxylases and biotin–carboxyl–carrier proteins," Arch. Microbiology (1996), 166, Nr. 2, pp. 76–82, XP–00957474.

Cremer, Josef et al., "Control of the Lysine Biosynthesis Sequence in Corynebacterium glutamicum as Analyzed by Overexpression of the Individual Corresponding Genes," Applied and Environmental Microbiology, Jun. 1991, pp. 1746–1752, XP–000616281.

Eggeling, L. et al, "Improved l–lysine yield with Corynebacterium glutamicum: use of dapA resulting in increased flux combined with growth limitation," Applied Microbiology and Biotechnology, Springer Verlag, Berlin, Germany (1998), 49, Nr. 1, pp. 24–30, XP–000918549.

Eikmans, Bernhard et al., "Molecular aspects of lysine, threonine, and isoleucine biosynthesis on Corynebacterium glutamicum," Antonie van Leeuwenhoek, Dordrecht, Netherlands (1993), 634, Nr. 2, pp. 145–163, XP–000918559.

Patek, M., et al., "Identification and transcriptional analysis of the dapB–ORF2–dap–A–ORF4 operon of Corynebacterium glutamicum, encoding two enzymes involved in L–lysine synthesis," Biotechnology Letters (Nov. 1997) 19, Nr. 11, pp. 1113–1117, XP–000956453.

*Primary Examiner*—Manjunath N. Rao
(74) *Attorney, Agent, or Firm*—Pillsbury Winthrop LLP

(57) ABSTRACT

The invention relates to nucleotide sequences coding for the accDA gene and to a process for the preparation of L-amino acids, especially L-lysine, by fermentation using corynebacteria in which the accDA gene is amplified.

20 Claims, 1 Drawing Sheet

US 6,808,914 B2

Figure 1:
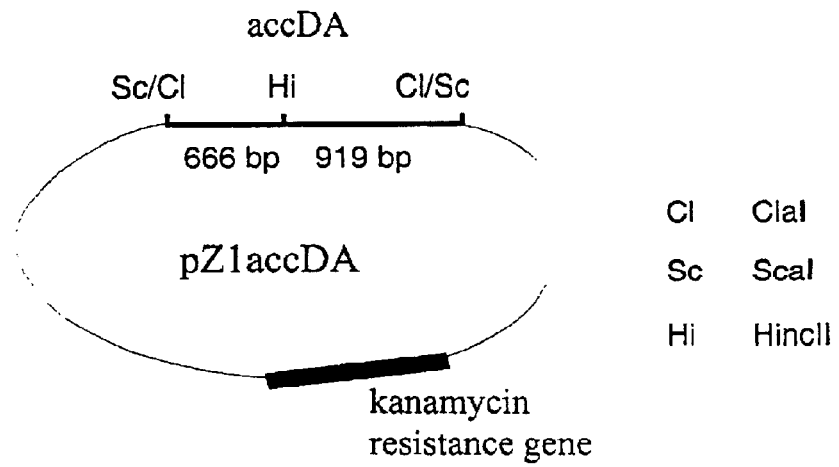

SEQUENCE LISTING

<160> NUMBER OF SEQ ID NOS: 3

<210> SEQ ID NO 1
<211> LENGTH: 2123
<212> TYPE: DNA
<213> ORGANISM: Corynebacterium glutamicum
<220> FEATURE:
<221> NAME/KEY: gene
<222> LOCATION: (508)..(1980)
<223> OTHER INFORMATION: accDA

<400> SEQUENCE: 1

| | | | | | |
|---|---|---|---|---|---|
| ctcgagcggg | agtcggtgat | cggccactct | ctaagcaatg | ccggctttaa | aataaagcaa | 60 |
| cttatatgtt | tctcaccaca | tctggccgac | gaccacgaag | tatgttgtcg | atcacagcta | 120 |
| aacgtgtgaa | tgtgaagtta | cctaactcac | attgcaatgc | gatagcgatt | tggaaaactc | 180 |
| actcccccca | atatcttaac | ttaaacttaa | aagtagtgtt | ttacctgcat | ttataaaagt | 240 |
| tcccgatcta | cccctctttt | accccgaaat | acccctttg | caaagattgc | aaacacaaca | 300 |
| gtgcaatagt | taacgggctt | cacacgtcac | cattctgtcc | ggttttaggc | tatgttcggg | 360 |
| acgtctaggc | aaaaagtagt | tttgtgagat | gaaacgcata | atccgtcatt | ttttacgcaa | 420 |
| tcgatagcct | aaattgggct | tagatcttcc | gcctctaaat | aggtatgcag | agacattcga | 480 |
| attaattaac | aaagccattt | tcggccgtg | gagaagcgtt | ttccgactat | ggtgtggggc | 540 |
| atggaacaca | cttcagcatt | gacgctcata | gactcggttt | tggaccctga | cagcttcatt | 600 |
| tcttggaatg | aaactcccca | atatgacaac | ctcaatcaag | gctatgcaga | gaccttggag | 660 |
| cgggctcgaa | gcaaggccaa | atgcgatgaa | tcggtaatta | ctggagaagg | caccgtggag | 720 |
| ggcattccgg | tagccgttat | tttgtccgat | ttttccttcc | tcggcggttc | tttgggcacg | 780 |
| gtcgcgtcgg | tgcgcatcat | gaaggcgatt | caccgcgcca | cagagctgaa | actcccactg | 840 |
| ctggtctccc | ctgcttccgg | tggtgcgcgc | atgcaggaag | acaatcgagc | ttttgtcatg | 900 |
| atggtgtcca | taccgcggc | tgtgcagcgt | caccgcgagg | cgcatttgcc | gttcctggtg | 960 |
| tatttgcgca | atcccacgat | gggtggcgcc | atggcctcgt | ggggttcatc | tgggcatctc | 1020 |
| acttttgcgg | aacccggcgc | gcagataggt | ttcctgggtc | ctcgcgtggt | ggagttaacc | 1080 |
| actgggcatg | cgcttccaga | cggtgtgcag | caggcggaga | atttggtgaa | aactggtgtg | 1140 |
| attgatggaa | ttgtgtcgcc | actccaattg | cgtgcagcgg | tggcaaaaac | cctcaaggtt | 1200 |
| attcagccgg | tagaggcaac | ggatcgtttt | tctccaacaa | ctcctggcgt | ggcacttccg | 1260 |
| gtgatggagg | cgattgcgcg | ttctcgtgac | ccgcagaggc | ctggaatcgg | ggagattatg | 1320 |
| gaaacgttgg | gggcagacgt | cgtcaagctt | tctggtgcgc | gtgctggcgc | attgagcccg | 1380 |
| gctgtgcgcg | ttgccctggc | gcgcatcggg | ggccggcccg | tggtgctgat | tgggcaggat | 1440 |
| cgccgcttca | cgcttgggcc | gcaggagctg | cgttttgcgc | gtcgtggcat | ttcgctggcg | 1500 |
| cgcgagctaa | acctgccgat | cgtgtccatc | atcgacacct | ccggcgccga | attgtcgcag | 1560 |
| gcggctgagg | agctcggcat | cgcaagctcg | attgcgcgca | ccttgtccaa | gcttatcgac | 1620 |
| gctcccctcc | ccaccgtttc | ggtcattatt | ggtcagggcg | ttggcggtgg | cgcgctggcc | 1680 |
| atgctgcccg | ccgatctggt | ctacgcggcc | gaaaacgcgt | ggctgtccgc | attgccacca | 1740 |
| gagggcgcct | cggccatcct | cttccgcgac | accaaccacg | ccgcggaaat | catagagcga | 1800 |
| caaggcgtgc | aggcgcacgc | acttttaagc | caagggctta | tcgacgggat | cgtcgccgaa | 1860 |
| accgagcact | tgttgaaga | aattctcggc | acaatcagca | acgccctctc | cgaattggat | 1920 |
| aacaatccgg | agagggcggg | acgcgacagt | cgcttcacac | gatttgagcg | tttagcgcag | 1980 |
| taaagaaaat | tatgcgctga | tcaaatcgat | gatgaacacc | agggtacggc | cagacagtgg | 2040 |
| gtggccggaa | ccctcaggc | cgtaagcagc | ctctggcgga | atggtcagct | gacgacgtcc | 2100 |
| gccgaccttc | atgcctggaa | ttc | | | | 2123 |

```
<210> SEQ ID NO 2
<211> LENGTH: 1473
<212> TYPE: DNA
<213> ORGANISM: Corynebacterium glutamicum
<220> FEATURE:
<221> NAME/KEY: CDS
<222> LOCATION: (1)..(1473)
<223> OTHER INFORMATION: accDA

<400> SEQUENCE: 2 gtg gag aag cgt ttt ccg act atg gtg tgg ggc atg gaa cac act tca      48
Val Glu Lys Arg Phe Pro Thr Met Val Trp Gly Met Glu His Thr Ser
 1               5                  10                  15 gca ttg acg ctc ata gac tcg gtt ttg gac cct gac agc ttc att tct      96
Ala Leu Thr Leu Ile Asp Ser Val Leu Asp Pro Asp Ser Phe Ile Ser
             20                  25                  30 tgg aat gaa act ccc caa tat gac aac ctc aat caa ggc tat gca gag     144
Trp Asn Glu Thr Pro Gln Tyr Asp Asn Leu Asn Gln Gly Tyr Ala Glu
         35                  40                  45 acc ttg gag cgg gct cga agc aag gcc aaa tgc gat gaa tcg gta att     192
Thr Leu Glu Arg Ala Arg Ser Lys Ala Lys Cys Asp Glu Ser Val Ile
     50                  55                  60 act gga gaa ggc acc gtg gag ggc att ccg gta gcc gtt att ttg tcc     240
Thr Gly Glu Gly Thr Val Glu Gly Ile Pro Val Ala Val Ile Leu Ser
 65                  70                  75                  80 gat ttt tcc ttc ctc ggc ggt tct ttg ggc acg gtc gcg tcg gtg cgc     288
Asp Phe Ser Phe Leu Gly Gly Ser Leu Gly Thr Val Ala Ser Val Arg
                 85                  90                  95 atc atg aag gcg att cac cgc gcc aca gag ctg aaa ctc cca ctg ctg     336
Ile Met Lys Ala Ile His Arg Ala Thr Glu Leu Lys Leu Pro Leu Leu
            100                 105                 110 gtc tcc cct gct tcc ggt ggt gcg cgc atg cag gaa gac aat cga gct     384
Val Ser Pro Ala Ser Gly Gly Ala Arg Met Gln Glu Asp Asn Arg Ala
        115                 120                 125 ttt gtc atg atg gtg tcc ata acc gcg gct gtg cag cgt cac cgc gag     432
Phe Val Met Met Val Ser Ile Thr Ala Ala Val Gln Arg His Arg Glu
    130                 135                 140 gcg cat ttg ccg ttc ctg gtg tat ttg cgc aat ccc acg atg ggt ggc     480
Ala His Leu Pro Phe Leu Val Tyr Leu Arg Asn Pro Thr Met Gly Gly
145                 150                 155                 160 gcc atg gcc tcg tgg ggt tca tct ggg cat ctc act ttt gcg gaa ccc     528
Ala Met Ala Ser Trp Gly Ser Ser Gly His Leu Thr Phe Ala Glu Pro
                165                 170                 175 ggc gcg cag ata ggt ttc ctg ggt cct cgc gtg gtg gag tta acc act     576
Gly Ala Gln Ile Gly Phe Leu Gly Pro Arg Val Val Glu Leu Thr Thr
            180                 185                 190 ggg cat gcg ctt cca gac ggt gtg cag cag gcg gag aat ttg gtg aaa     624
Gly His Ala Leu Pro Asp Gly Val Gln Gln Ala Glu Asn Leu Val Lys
        195                 200                 205 act ggt gtg att gat gga att gtg tcg cca ctc caa ttg cgt gca gcg     672
Thr Gly Val Ile Asp Gly Ile Val Ser Pro Leu Gln Leu Arg Ala Ala
    210                 215                 220 gtg gca aaa acc ctc aag gtt att cag ccg gta gag gca acg gat cgt     720
Val Ala Lys Thr Leu Lys Val Ile Gln Pro Val Glu Ala Thr Asp Arg
225                 230                 235                 240 ttt tct cca aca act cct ggc gtg gca ctt ccg gtg atg gag gcg att     768
Phe Ser Pro Thr Thr Pro Gly Val Ala Leu Pro Val Met Glu Ala Ile
                245                 250                 255 gcg cgt tct cgt gac ccg cag agg cct gga atc ggg gag att atg gaa     816
Ala Arg Ser Arg Asp Pro Gln Arg Pro Gly Ile Gly Glu Ile Met Glu
            260                 265                 270
```

-continued

| | | | | | | | | | | | | | | | |
|---|---|---|---|---|---|---|---|---|---|---|---|---|---|---|---|
| acg | ttg | ggg | gca | gac | gtc | gtc | aag | ctt | tct | ggt | gcg | cgt | gct | ggc | gca | 864 |
| Thr | Leu | Gly | Ala | Asp | Val | Val | Lys | Leu | Ser | Gly | Ala | Arg | Ala | Gly | Ala | |
| | | 275 | | | | 280 | | | | | 285 | | | | | |
| ttg | agc | ccg | gct | gtg | cgc | gtt | gcc | ctg | gcg | cgc | atc | ggg | ggc | cgg | ccc | 912 |
| Leu | Ser | Pro | Ala | Val | Arg | Val | Ala | Leu | Ala | Arg | Ile | Gly | Gly | Arg | Pro | |
| | 290 | | | | | 295 | | | | 300 | | | | | | |
| gtg | gtg | ctg | att | ggg | cag | gat | cgc | cgc | ttc | acg | ctt | ggg | ccg | cag | gag | 960 |
| Val | Val | Leu | Ile | Gly | Gln | Asp | Arg | Arg | Phe | Thr | Leu | Gly | Pro | Gln | Glu | |
| 305 | | | | | 310 | | | | | 315 | | | | | 320 | |
| ctg | cgt | ttt | gcg | cgt | cgt | ggc | att | tcg | ctg | gcg | cgc | gag | cta | aac | ctg | 1008 |
| Leu | Arg | Phe | Ala | Arg | Arg | Gly | Ile | Ser | Leu | Ala | Arg | Glu | Leu | Asn | Leu | |
| | | | | 325 | | | | | 330 | | | | | 335 | | |
| ccg | atc | gtg | tcc | atc | atc | gac | acc | tcc | ggc | gcc | gaa | ttg | tcg | cag | gcg | 1056 |
| Pro | Ile | Val | Ser | Ile | Ile | Asp | Thr | Ser | Gly | Ala | Glu | Leu | Ser | Gln | Ala | |
| | | | 340 | | | | | 345 | | | | | 350 | | | |
| gct | gag | gag | ctc | ggc | atc | gca | agc | tcg | att | gcg | cgc | acc | ttg | tcc | aag | 1104 |
| Ala | Glu | Glu | Leu | Gly | Ile | Ala | Ser | Ser | Ile | Ala | Arg | Thr | Leu | Ser | Lys | |
| | | 355 | | | | 360 | | | | | 365 | | | | | |
| ctt | atc | gac | gct | ccc | ctc | ccc | acc | gtt | tcg | gtc | att | att | ggt | cag | ggc | 1152 |
| Leu | Ile | Asp | Ala | Pro | Leu | Pro | Thr | Val | Ser | Val | Ile | Ile | Gly | Gln | Gly | |
| | 370 | | | | | 375 | | | | 380 | | | | | | |
| gtt | ggc | ggt | ggc | gcg | ctg | gcc | atg | ctg | ccc | gcc | gat | ctg | gtc | tac | gcg | 1200 |
| Val | Gly | Gly | Gly | Ala | Leu | Ala | Met | Leu | Pro | Ala | Asp | Leu | Val | Tyr | Ala | |
| 385 | | | | | 390 | | | | | 395 | | | | | 400 | |
| gcc | gaa | aac | gcg | tgg | ctg | tcc | gca | ttg | cca | cca | gag | ggc | gcc | tcg | gcc | 1248 |
| Ala | Glu | Asn | Ala | Trp | Leu | Ser | Ala | Leu | Pro | Pro | Glu | Gly | Ala | Ser | Ala | |
| | | | | 405 | | | | | 410 | | | | | 415 | | |
| atc | ctc | ttc | cgc | gac | acc | aac | cac | gcc | gcg | gaa | atc | ata | gag | cga | caa | 1296 |
| Ile | Leu | Phe | Arg | Asp | Thr | Asn | His | Ala | Ala | Glu | Ile | Ile | Glu | Arg | Gln | |
| | | | 420 | | | | | 425 | | | | | 430 | | | |
| ggc | gtg | cag | gcg | cac | gca | ctt | tta | agc | caa | ggg | ctt | atc | gac | ggg | atc | 1344 |
| Gly | Val | Gln | Ala | His | Ala | Leu | Leu | Ser | Gln | Gly | Leu | Ile | Asp | Gly | Ile | |
| | | 435 | | | | 440 | | | | | 445 | | | | | |
| gtc | gcc | gaa | acc | gag | cac | ttt | gtt | gaa | gaa | att | ctc | ggc | aca | atc | agc | 1392 |
| Val | Ala | Glu | Thr | Glu | His | Phe | Val | Glu | Glu | Ile | Leu | Gly | Thr | Ile | Ser | |
| | 450 | | | | | 455 | | | | 460 | | | | | | |
| aac | gcc | ctc | tcc | gaa | ttg | gat | aac | aat | ccg | gag | agg | gcg | gga | cgc | gac | 1440 |
| Asn | Ala | Leu | Ser | Glu | Leu | Asp | Asn | Asn | Pro | Glu | Arg | Ala | Gly | Arg | Asp | |
| 465 | | | | | 470 | | | | | 475 | | | | | 480 | |
| agt | cgc | ttc | aca | cga | ttt | gag | cgt | tta | gcg | cag | | | | | | 1473 |
| Ser | Arg | Phe | Thr | Arg | Phe | Glu | Arg | Leu | Ala | Gln | | | | | | |
| | | | | 485 | | | | | 490 | | | | | | | |

<210> SEQ ID NO 3
<211> LENGTH: 491
<212> TYPE: PRT
<213> ORGANISM: Corynebacterium glutamicum

<400> SEQUENCE: 3

Val Glu Lys Arg Phe Pro Thr Met Val Trp Gly Met Glu His Thr Ser
 1               5                  10                  15

Ala Leu Thr Leu Ile Asp Ser Val Leu Asp Pro Asp Ser Phe Ile Ser
            20                  25                  30

Trp Asn Glu Thr Pro Gln Tyr Asp Asn Leu Asn Gln Gly Tyr Ala Glu
        35                  40                  45

Thr Leu Glu Arg Ala Arg Ser Lys Ala Lys Cys Asp Glu Ser Val Ile
    50                  55                  60

Thr Gly Glu Gly Thr Val Glu Gly Ile Pro Val Ala Val Ile Leu Ser
65                  70                  75                  80

-continued

```
Asp Phe Ser Phe Leu Gly Gly Ser Leu Gly Thr Val Ala Ser Val Arg
                85                  90                  95

Ile Met Lys Ala Ile His Arg Ala Thr Glu Leu Lys Leu Pro Leu Leu
            100                 105                 110

Val Ser Pro Ala Ser Gly Gly Ala Arg Met Gln Asp Asn Arg Ala
        115                 120                 125

Phe Val Met Met Val Ser Ile Thr Ala Ala Val Gln Arg His Arg Glu
    130                 135                 140

Ala His Leu Pro Phe Leu Val Tyr Leu Arg Asn Pro Thr Met Gly Gly
145                 150                 155                 160

Ala Met Ala Ser Trp Gly Ser Ser Gly His Leu Thr Phe Ala Glu Pro
                165                 170                 175

Gly Ala Gln Ile Gly Phe Leu Gly Pro Arg Val Val Glu Leu Thr Thr
                180                 185                 190

Gly His Ala Leu Pro Asp Gly Val Gln Gln Ala Glu Asn Leu Val Lys
            195                 200                 205

Thr Gly Val Ile Asp Gly Ile Val Ser Pro Leu Gln Leu Arg Ala Ala
    210                 215                 220

Val Ala Lys Thr Leu Lys Val Ile Gln Pro Val Glu Ala Thr Asp Arg
225                 230                 235                 240

Phe Ser Pro Thr Thr Pro Gly Val Ala Leu Pro Val Met Glu Ala Ile
                245                 250                 255

Ala Arg Ser Arg Asp Pro Gln Arg Pro Gly Ile Gly Glu Ile Met Glu
                260                 265                 270

Thr Leu Gly Ala Asp Val Val Lys Leu Ser Gly Ala Arg Ala Gly Ala
            275                 280                 285

Leu Ser Pro Ala Val Arg Val Ala Leu Ala Arg Ile Gly Gly Arg Pro
    290                 295                 300

Val Val Leu Ile Gly Gln Asp Arg Arg Phe Thr Leu Gly Pro Gln Glu
305                 310                 315                 320

Leu Arg Phe Ala Arg Arg Gly Ile Ser Leu Ala Arg Glu Leu Asn Leu
                325                 330                 335

Pro Ile Val Ser Ile Asp Thr Ser Gly Ala Glu Leu Ser Gln Ala
                340                 345                 350

Ala Glu Glu Leu Gly Ile Ala Ser Ser Ile Ala Arg Thr Leu Ser Lys
            355                 360                 365

Leu Ile Asp Ala Pro Leu Pro Thr Val Ser Val Ile Ile Gly Gln Gly
    370                 375                 380

Val Gly Gly Gly Ala Leu Ala Met Leu Pro Ala Asp Leu Val Tyr Ala
385                 390                 395                 400

Ala Glu Asn Ala Trp Leu Ser Ala Leu Pro Pro Glu Gly Ala Ser Ala
                405                 410                 415

Ile Leu Phe Arg Asp Thr Asn His Ala Ala Glu Ile Ile Glu Arg Gln
                420                 425                 430

Gly Val Gln Ala His Ala Leu Leu Ser Gln Gly Leu Ile Asp Gly Ile
            435                 440                 445

Val Ala Glu Thr Glu His Phe Val Glu Glu Ile Leu Gly Thr Ile Ser
    450                 455                 460

Asn Ala Leu Ser Glu Leu Asp Asn Asn Pro Glu Arg Ala Gly Arg Asp
465                 470                 475                 480

Ser Arg Phe Thr Arg Phe Glu Arg Leu Ala Gln
                485                 490
```

PROCESS FOR THE PREPARATION OF L-AMINO ACIDS BY FERMENTATION AND NUCLEOTIDE SEQUENCES CODING FOR THE ACCDA GENE

This is a divisional of U.S. patent application Ser. No. 09/362,899, filed Jul. 29, 1999, now U.S. Pat. No. 6,361, 986, which claims priority to German Patent Appl. No. 199 24 365.4 filed May 27, 1999, the subject matter both of which is hereby incorporated herein by reference.

The invention provides nucleotide sequences coding for the accDA gene and a process for the preparation of L-amino acids, especially L-lysine, by fermentation using corynebacteria in which the accDA gene is amplified.

STATE OF THE ART

L-Amino acids, especially L-lysine, are used in animal nutrition, in human medicine and in the pharmaceutical industry.

It is known that these amino acids are prepared by the fermentation of strains of corynebacteria, especially *Corynebacterium glutamicum*. Because of their great importance, attempts are constantly being made to improve the preparative processes. Improvements to the processes may relate to measures involving the fermentation technology, e.g. stirring and oxygen supply, or the composition of the nutrient media, e.g. the sugar concentration during fermentation, or the work-up to the product form, e.g. by ion exchange chromatography, or the intrinsic productivity characteristics of the microorganism itself.

The productivity characteristics of these microorganisms are improved by using methods of mutagenesis, selection and mutant choice to give strains which are resistant to antimetabolites, e.g. the lysine analog S-(2-aminoethyl) cysteine, or auxotrophic for amino acids of regulatory significance, and produce L-amino acids.

Methods of recombinant DNA technology have also been used for some years in order to improve L-amino acid-producing strains of *Corynebacterium* by amplifying individual amino acid biosynthesis genes and studying the effect on L-lysine production. Surveys of this subject have been published inter alia by Kinoshita ("Glutamic Acid Bacteria" in: Biology of Industrial Microorganisms, Demain and Solomon (Eds.), Benjamin Cummings, London, UK, 1985, 115–142), Hilliger (BioTec 2, 40–44 (1991)), Eggeling (Amino Acids 6, 261–272 (1994)), Jetten and Sinskey (Critical Reviews in Biotechnology 15, 73–103 (1995)) and Sahm et al. (Annuals of the New York Academy of Science 782, 25–39 (1996)).

The enzyme acetyl-CoA carboxylase catalyzes the carboxylation of acetyl-CoA to malonyl-CoA. The enzyme from *Escherichia coli* consists of four subunits. The accB gene codes for biotin carboxyl carrier protein, the accC gene for biotin carboxylase and the accA and accD genes for transcarboxylase (Cronan and Rock, Biosynthesis of Membrane Lipids, in: *Escherichia coli* and *Salmonella typhimurium* (ed. F. C. Neidhardt), 1996, pp. 612–636, American Society for Microbiology). Because of the property of the enzyme to carboxylate acyl groups in the form of acyl-CoA, it is also called acyl-CoA carboxylase.

The nucleotide sequence of the accBC gene from *Corynebacterium glutamicum* has been determined by Jäger et al. (Archives of Microbiology 166, 76–82 (1996)) and is generally available from the data bank of the European Molecular Biologies Laboratories (EMBL, Heidelberg, Germany) under accession number U35023. The accBC gene codes for a subunit of acetyl-CoA carboxylase which carries a biotin carboxyl carrier protein domain and a biotin carboxylase domain.

OBJECT OF THE INVENTION

The object which the inventors set themselves was to provide novel procedures for the improved preparation of L-amino acids, especially L-lysine, by fermentation.

DESCRIPTION OF THE INVENTION

L-Amino acids are used in animal nutrition, in human medicine and in the pharmaceutical industry. It is therefore of general interest to provide novel improved processes for the preparation of L-amino acids.

When L-lysine or lysine is mentioned in the following text, it is understood as meaning not only the base but also the salts, e.g. lysine monohydrochloride or lysine sulfate.

The invention provides a preferably recombinant DNA originating from *Corynebacterium* which is capable of replication in coryneform microorganisms and which at least contains the nucleotide sequence coding for the accDA gene shown in SEQ ID No. 1.

The invention also provides a DNA capable of replication, as claimed in claim 1, with:

(i) the nucleotide sequence shown in SEQ ID No. 1, (ii) at least one sequence corresponding to the sequence
(i) within the region of degeneracy of the genetic code, or (iii) at least one sequence hybridizing with the sequence complementary to the sequence (i) or (ii), and optionally (vi) [sic] neutral sense mutations in (i).

The invention also provides coryneform microorganisms, especially of the genus *Corynebacterium*, transformed by the introduction of said DNA capable of replication.

The invention further relates to a process for the preparation of L-amino acids by fermentation using corynebacteria which, in particular, already produce the L-amino acids and in which the nucleotide sequences coding for the accDA gene are amplified and, in particular, overexpressed.

Finally, the invention also provides a process for the amplification of acyl-CoA carboxylase in corynebacteria by joint overexpression of the novel accDA gene according to the invention and the known accBC gene.

In this context the term "samplification" describes the increase in the intracellular activity, in a microorganism, of one or more enzymes which are coded for by the appropriate DNA, for example by increasing the copy number of the gene(s), using a strong promoter or using a gene coding for an appropriate enzyme with a high activity, and optionally combining these measures.

The microorganisms which the present invention provides can produce L-amino acids from glucose, sucrose, lactose, fructose, maltose, molasses, starch or cellulose or from glycerol and ethanol. Said microorganisms can be representatives of corynebacteria, especially of the genus *Corynebacterium*. The species *Corynebacterium glutamicum* may be mentioned in particular in the genus *Corynebacterium*, being known to those skilled in the art for its ability to produce L-amino acids.

Suitable strains of the genus *Corynebacterium*, especially of the species *Corynebacterium glutamicum*, are the known wild-type strains:

*Corynebacterium glutamicum* ATCC13032

*Corynebacterium acetoglutamicum* ATCC15806

*Corynebacterium acetoacidophilum* ATCC13870
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020
and L-amino acid-producing mutants or strains prepared therefrom, for example:
*Corynebacterium glutamicum* FERM-P1709
*Brevibacterium flavum* FERM-P1708
*Brevibacterium lactofermentum* FERM-P1712
*Corynebacterium glutamicum* FERM-P6463 and
*Corynebacterium glutamicum* FERM-P6464

The inventors have succeeded in isolating the novel accDA gene from *C. glutamicum*. The accDA gene or other genes are isolated from *C. glutamicum* by first constructing a gene library of this microrganism [sic] in *E. coli*. The construction of gene libraries is documented in generally well-known textbooks and handbooks. Examples which may be mentioned are the textbook by Winnacker entitled From Genes to Clones, Introduction to Gene Technology (Verlag Chemie, Weinheim, Germany, 1990) or the handbook by Sambrook et al. entitled Molecular Cloning, A Laboratory Manual (Cold Spring Harbor Laboratory Press, 1989). A very well-known gene library is that of the *E. coli* K-12 strain W3110 constructed by Kohara et al. (Cell 50, 495–508 (1987)) in λ vectors. Bathe et al. (Molecular and General Genetics 252, 255–265 (1996)) describe a gene library of *C. glutamicum* ATCC13032 constructed using cosmid vector SuperCos I (Wahl et al., Proceedings of the National Academy of Sciences USA 84, 2160–2164 (1987)) in the *E. coli* K-12 strain NM554 (Raleigh et al., Nucleic Acids Research 16, 1563–1575 (1988)). Börmann et al. (Molecular Microbiology 6(3), 317–326) in turn describe a gene library of *C. glutamicum* ATCC13032 using cosmid pHC79 (Hohn and Collins, Gene 11, 291–298 (1980)). A gene library of *C. glutamicum* in *E. coli* can also be constructed using plasmids like pBR322 (Bolivar, Life Sciences 25, 807–818 (1979)) or pUC9 (Viera et al., Gene 19, 259–268 (1982)). Restriction- and recombination-defective *E. coli* strains are particularly suitable hosts, an example being the strain DH5αmcr described by Grant et al. (Proceedings of the National Academy of Sciences USA 87, 4645–4649 (1990)). The long DNA fragments cloned using cosmids can then in turn be subcloned into common vectors suitable for sequencing, and subsequently sequenced, e.g. as described by Sanger et al. (Proceedings of the National [sic] of Sciences of the United States of America [sic] USA 74, 5463–5467 (1977)).

The novel DNA sequence from *C. glutamicum* coding for the accDA gene was obtained in this way and, as SEQ ID No. 1, is part of the present invention. The coding region (cds) of the accDA gene is shown in SEQ ID No. 2. The amino acid sequence of the corresponding protein was also derived from the present DNA sequence by the methods described above. The resulting amino acid sequence of the accDA gene product is shown in SEQ ID No. 3.

Coding DNA sequences which result from SEQ ID No. 1 due to the degeneracy of the genetic code are also part of the invention. Similarly, DNA sequences which hybridize with SEQ ID No. 1 or sections of SEQ ID No. 1 are part of the invention. Furthermore, conservative amino acid exchanges, e.g. the exchange of glycine for alanine or of aspartic acid for glutamic acid in proteins, are known to those skilled in the art as sense mutations, which do not cause a fundamental change in the activity of the protein, i.e. they are neutral. It is also known that changes at the N and/or C terminus of a protein do not substantially impair its function or can even stabilize it. Those skilled in the art will find information on this subject inter alia in Ben-Bassat et al. (Journal of Bacteriology 169, 751–757 (1987)), O'Regan et al. (Gene 77, 237–251 (1989)), Sahin-Tóth et al. (Protein Sciences 3, 240–247 (1994)), Hochuli et al. (Bio/Technology 6, 1321–1325 (1988)) and well-known textbooks on genetics and molecular biology. Amino acid sequences which correspondingly result from SEQ ID No. 3 are also part of the invention.

The inventors have found that overexpression of the accDA genes in corynebacteria improves L-lysine production.

An overexpression can be achieved by increasing the copy number of the appropriate genes or mutating the promoter and regulatory region or the ribosome binding site located upstream from the structural gene. Expression cassettes incorporated upstream from the structural gene work in the same way. Inducible promoters additionally make it possible to increase the expression in the course of L-lysine production by fermentation. Measures for prolonging the life of the mRNA also improve the expression. Furthermore, the enzyme activity is also enhanced by preventing the degradation of the enzyme protein. The genes or gene constructs can either be located in plasmids of variable copy number or be integrated and amplified in the chromosome. Alternatively, it is also possible to achieve an overexpression of the genes in question by changing the composition of the media and the culture technique.

Those skilled in the art will find appropriate instructions inter alia in Martin et al. (Bio/Technology 5, 137–146 (1987)), Guerrero et al. (Gene 138, 35–41 (1994)), Tsuchiya and Morinaga (Bio/Technology 6, 428–430 (1988)), Eikmanns et al. (Gene 102, 93–98 (1991)), EP 0 472 869, U.S. Pat. No. 4,601,893, Schwarzer and Pühler (Bio/Technology 9, 84–87 (1991)), Reinscheid et al. (Applied and Environmental Microbiology 60, 126–132 (1994)), LaBarre et al. (Journal of Bacteriology 175, 1001–1007 (1993)), patent application WO 96/15246, Malumbres et al. (Gene 134, 15–24 (1993)), Japanese Offenlegungsschrift JP-A-10-229891, Jensen and Hammer (Biotechnology and Bioengineering 58, 191–195 (1998)), Makrides (Microbiological Reviews 60, 512–538 (1996)) and well-known textbooks on genetics and molecular biology.

An example of a plasmid by means of which the accDA gene can be overexpressed is pZ1accDA (FIG. 1), which is contained in the strain MH20-22B/pZ1accDA. Plasmid pZ1accDA is an *E. coli-C. glutamicum* shuttle vector which carries the accDA gene and is based on plasmid pZ1(Menkel et al., Applied and Environmental Microbiology 55(3), 684–688 (1989)). Other plasmid vectors capable of replication in *C. glutamicum*, e.g. pEKEx1(Eikmanns et al., Gene 102, 93–98 (1991)) or pZ8-1 (EP 0 375 889), can be used in the same way.

Figure 2:
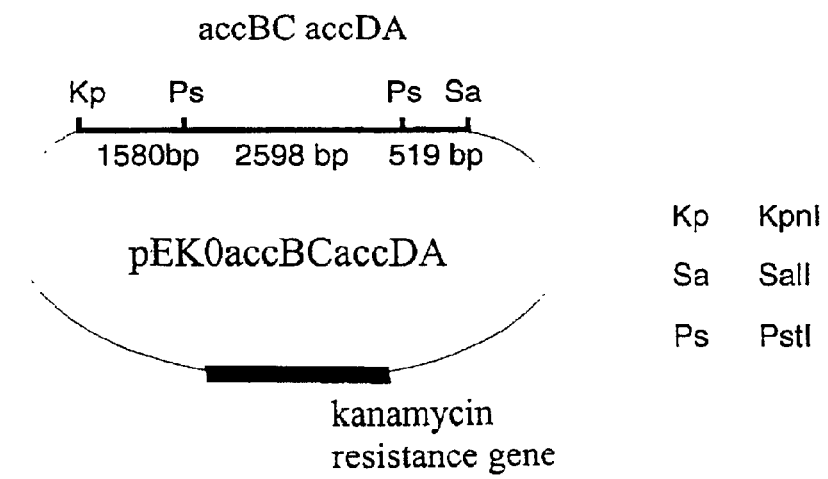

The inventors have also found that overexpression of the known accBC gene in addition to the novel accDA gene according to the invention in corynebacteria improves acyl-CoA carboxylase production. An example of a plasmid by means of which the accDA gene and the accBC gene can be jointly overexpressed is pEK0accBCaccDA (FIG. 2). Plasmid pEK0accBCaccDA is an *E. coli-C. glutamicum* shuttle vector which carries the accBC and accDA genes and is based on plasmid pEK0 (Eikmanns et al., Gene 102, 93–98 (1991)). Other plasmid vectors capable of replication in *C. glutamicum*, e.g. pEKEx1 (Eikmanns et al., Gene 102, 93–98 (1991)) or pZ8-1 (EP 0 375 889), can be used in the same way.

In addition, it can be advantageous for L-amino acid production to overexpress not only the accDA gene but also one or more enzymes of the biosynthetic pathway. Thus it is possible, for example for the preparation of L-lysine, simultaneously to overexpress the dapa gene coding for dihydrodipicolinate synthase (EP-B 0 197 335), or simultaneously to amplify a DNA fragment conferring S-(2-aminoethyl) cysteine resistance (EPA 0 088 166).

Furthermore, it can be advantageous for the production of L-amino acids, especially L-lysine, to switch off undesirable secondary reactions as well as overexpress the accDA gene (Nakayama: "Breeding of Amino acid-Producing Microorganisms" in: Overproduction of Microbial Products, Krumphanzl, Sikyta, Vanek (eds.), Academic Press, London, UK, 1982).

The microorganisms prepared according to the invention can be cultivated for L-lysine production continuously or discontinuously by the batch process, the fed batch process or the repeated fed batch process. A summary of known cultivation methods is provided in the textbook by Chmiel (Bioprozesstechnik 1. Einführung in die Bioverfahrenstechnik (Bioprocess Technology 1. Introduction to Bioengineering) (Gustav Fischer Verlag, Stuttgart, 1991)) or in the textbook by Storhas (Bioreaktoren und periphere Einrichtungen (Bioreactors and Peripheral Equipment) (Vieweg Verlag, Brunswick/Wiesbaden, 1994)).

The culture medium to be used must appropriately meet the demands of the particular strains. Descriptions of culture media for various microorganisms can be found in the handbook "Manual of Methods for General Bacteriology" of the American Society for Bacteriology (Washington DC, USA, 1981). Carbon sources which can be used are sugars and carbohydrates, e.g. glucose, sucrose, lactose, fructose, maltose, molasses, starch and cellulose, oils and fats, e.g. soya oil, sunflower oil, groundnut oil and coconut fat, fatty acids, e.g. palmitic acid, stearic acid and linoleic acid, alcohols, e.g. glycerol and ethanol, and organic acids, e.g. acetic acid. These substances can be used individually or as a mixture. Nitrogen sources which can be used are organic nitrogen-containing compounds such as peptones, yeast extract, meat extract, malt extract, corn steep liquor, soybean flour and urea, or inorganic compounds such as ammonium sulfate, ammonium chloride, ammonium phosphate, ammonium carbonate and ammonium nitrate. The nitrogen sources can be used individually or as a mixture. Phosphorus sources which can be used are phosphoric acid, potassium dihydrogenphosphate or dipotassium hydrogenphosphate or the corresponding sodium salts. The culture medium must also contain metal salts, e.g. magnesium sulfate or iron sulfate, which are necessary for growth. Finally, essential growth-promoting substances such as amino acids and vitamins can be used in addition to the substances mentioned above. Suitable precursors can also be added to the culture medium. Said feed materials can be added to the culture all at once or fed in appropriately during cultivation.

The pH of the culture is controlled by the appropriate use of basic compounds such as sodium hydroxide, potassium hydroxide, ammonia or aqueous ammonia, or acid compounds such as phosphoric acid or sulfuric acid. Foaming can be controlled using antifoams such as fatty acid polyglycol esters. The stability of plasmids can be maintained by adding suitable selectively acting substances, e.g. antibiotics, to the medium. Aerobic conditions are maintained by introducing oxygen or oxygen-containing gaseous mixtures, e.g. air, into the culture. The temperature of the culture is normally 20° C. to 45° C. and preferably 25° C. to 40° C. The culture is continued until formation of the desired L-amino acid has reached a maximum. This objective is normally achieved within 10 hours to 160 hours.

L-Lysine can be analyzed takes place [sic] by means of anion exchange chromatography followed by ninhydrin derivatization, as described by Spackman et al. (Analytical Chemistry 30, 1190 (1958)).

The following microorganisms have been deposited in the Deutsche Sammlung Von Mikrorganismen und Zellkulturen ((DSMZ-German Collection of Microrganisms and Cell Cultures (DSMZ), Mascheroder Weg 1b, D-38124 Braunschweig, Brunswick, Germany) under the terms of the Budapest Treaty:

Corynebacterium glutamicum strain DSM5715/pZ1accDA as DSM12785

Corynebacterium glutamicum strain DSM5715/pEK0accBCaccDA as DSM12787

The process according to the invention is used for the preparation of L-amino acids, especially L-aspartic acid, L-asparagine, L-homoserine, L-threonine, L-isoleucine and L-methionine, by the fermentation of corynebacteria. It is used particularly for the preparation of L-lysine.

EXAMPLES

The present invention is illustrated in greater detail below with the aid of Examples.

Example 1

Cloning and sequencing of the accDA gene

A gene library of *C. glutamicum* ATCC13032 was constructed using cosmid pHC79 (Hohn and Collins, Gene 11, 291–298 (1980)), as described by Börmann et al. (Molecular Microbiology 6(3), 317–326).

A chosen cosmid was digested with the restriction enzymes EcoRI and XhoI as instructed by the manufacturer of these restriction enzymes (Boehringer Mannheim). The DNA fragments formed were mixed with vector pUC18 (Norrander et al., Gene 26, 101–106 (1983)), which had also been treated with the restriction enzymes EcoRI and XhoI, and, after treatment with T4 DNA ligase, were cloned into the *E. coli* strain DH5αmcr (Grant et al., Proceedings of the National Academy of Sciences USA 87, 4645–4645 [sic] (1990)), as described by Sambrook et al. (Molecular Cloning, a Laboratory Manual (1989), Cold Spring Harbor Laboratories). The transformants were selected on LB agar containing 50 μg/ml of ampicillin, as described by Sambrook et al. (Molecular Cloning, a Laboratory Manual (1989), Cold Spring Harbor Laboratories). Plasmid DNA was isolated from a transformant and called pUCaccDA. Subclones were then prepared, via exonuclease III digestion, using the kit (Erase-a-Base) provided for this purpose by Promega (Heidelberg, Germany). Said subclones were sequenced by the dideoxy chain termination method of Sanger et al. (Proceedings of the National Academy of Sciences USA 74, 5463–5467 (1977)). This was done using the Auto-Read Sequencing Kit (Amersham Pharmacia Biotech, Uppsala, Sweden). Gel electrophoretic analysis was carried out with the automatic laser fluorescence (A.L.F.) sequencer from Amersham Pharmacia Biotech (Uppsala, Sweden). The nucleotide sequence obtained was analyzed with the HUSAR software package (Release 4.0, EMBL, Heidelberg, Germany). The nucleotide sequence is shown in SEQ ID No. 1. Analysis of the nucleotide sequence showed an open reading frame of 1473 base pairs, which was called the accDA gene. The accDA gene from *C. glutamicum* codes for a polypeptide of 484 amino acids.

Example 2

Expression of the and accDA gene in *Corynebacterium glutamicum*

The accDA gene was subcloned into vector pZ1(Menkel et al., Applied and Environmental Microbiology 55, 684–688 (1989)) for expression in *C. glutamicum*. This was done by cleaving plasmid pUCaccDA (cf. Example 1) with the restriction enzyme ClaI. The resulting 1.6 kb fragment was isolated as described in Example 1, treated with Klenow polymerase and alkaline phosphatase and used for ligation to pZ1, said vector having been linearized with ScaI beforehand. The ligation mixture was used to transform *E. coli* DH5αmcr (Grant et al., Proceedings of the National Academy of Sciences USA 87, 4645–4645 [sic] (1990)) and transformants were selected on LB agar containing kanamycin (50 μg/ml) to give the 7.7 kb shuttle vector pZ1accDA (FIG. 1). This was incorporated into the strain DSM5715 by means of electroporation, as described by Haynes (FEMS Microbiol. Letters 61, 329–334 (1989)), and the transformants were selected on LBHIS agar (Liebl et al., FEMS Microbiology Letters 65, 299–304 (1989)) to give the *C. glutamicum* strain DSM5715/pZ1accDA.

Example 3

Preparation of L-lysine with the strain DSM5715/pZ1accDA

After precultivation in medium CgIII (Keilhauer et al., Journal of Bacteriology 175, 5595–5603 (1993)), the strain DSM5715/pZ1accDA was cultivated in production medium CgXII (Keilhauer et al., Journal of Bacteriology 175, 5595–5603 (1993)). 4% of glucose and 50 mg/l of kanamycin sulfate were added.

After incubation for 48 hours, the optical density at 660 nm and the concentration of L-lysine formed were determined. The experimental results are shown in Table 1.

TABLE 1

| Strain | OD | L-Lysine g/l |
|---|---|---|
| DSM5175 [sic] | 31.4 | 7.2 |
| DSM5715/pZ1accDA | 43.1 | 8.0 |

Example 4

Joint expression of accBC and accDA (i) Construction of expression vector pEK0accBCaccDA Plasmid pWJ71 containing accBC (Jäger et al., Archives of Microbiology 166, 76–82 (1996)) was digested with the restriction enzymes AgeI and SmaI and then treated with Klenow polymerase and alkaline phosphatase. In a parallel operation, plasmid pUCaccDA was digested [sic] EcoRI/XhoI and then treated with Klenow polymerase and alkaline phosphatase. The 2.1 kb fragment carrying accDA was isolated by preparative isolation from an agarose gel, which was carried out as described by Sambrook et al. (Molecular Cloning, a Laboratory Manual (1989), Cold Spring Harbor Laboratories). Said fragment was ligated to vector pWJ71, which had been prepared as described above. The 4.6 kb fragment carrying accBCaccDA was cleaved from the resulting plasmid by KpnI/SalI digestion and again isolated by preparative agarose gel electrophoresis. To ligate this fragment to *C. glutamicum/E. coli* shuttle vector pEK0 (Eikmanns et al., Gene 102, 93–98 (1991)), pEK0 was digested with the restriction enzymes KpnI and SalI and then treated with Klenow polymerase and alkaline phosphatase. The vector prepared in this way was ligated to the 4.6 kb fragment carrying accBCaccDA. The resulting vector pEK0accBCaccDA is shown in FIG. 2. This vector was incorporated into the strain ATCC13032 by means of electroporation (Haynes, FEMS Microbiol. Letters 61, 329–334 (1969)), as described in Example 2, to give the *C. glutamicum* strain ATCC13032/pEK0accBCaccDA.

(ii) Determination of the acyl-CoA carboxylase activity After preculture in medium CGIII (Keilhauer et al., Journal of Bacteriology 175, 5595–5603 (1993)), the strain *C. glutamicum* ATCC13032/pEK0accBCaccDA was grown in medium CGXII, which is described by Keilhauer et al. (Journal of Bacteriology 175, 5595–5603 (1993)). The cells were harvested by centrifugation and the cell pellet was washed once with 60 mM Tris-HCl (pH 7.2) and resuspended in the same buffer. The cells were digested by means of a 10-minute ultrasound treatment (Branson sonifier W-250, Branson Sonic Power Co., Danbury, USA). The cell debris was then separated off by centrifugation for 30 minutes at 4° C. and the supernatant was used as crude extract in the enzyme test. The reaction mixture for the enzyme test contained 60 mM Tris-HCl (pH 7.2 ), 65 mM $KHCO_3$, 1 mM ATP, 1.5 mM $MgCl_2$, 4 mM acyl-CoA (choice of acetyl-CoA or propionyl-CoA) and 4 mg of crude extract in a reaction volume of 1 ml. The test mixtures were incubated at 30° C., 100 μl samples were taken after 15, 30, 45 and 60 seconds and their concentration of malonyl-CoA or methylmalonyl-CoA was determined by means of HPLC analysis (Kimura et al., Journal of Bacteriology 179, 7098–7102 (1997)). As shown in Table 2, the strain *C. glutamicum* ATCC13032/pEK0accBCaccDA exhibits a high acyl-CoA carboxylase activity with both acetyl-CoA and propionyl-CoA, whereas the control strain has only a low acyl-CoA carboxylase activity with both acetyl-CoA and propionyl-CoA.

TABLE 2

Specific acyl-CoA carboxylase activity (μmol/min and mg protein) in *C. glutamicum*

| Strian | Acyl-CoA carboxylase activity with the substrate | |
|---|---|---|
| | acetyl-CoA | propionyl-CoA |
| ATCC13032/pEK0accBCaccDA | 0 048 | 0.124 |
| ATCC13032/pEK0 | 0.011 | 0.018 |

The following Figures are attached:

FIG. 1: Map of plasmid pZ1accDA

FIG. 2: Map of plasmid pEK0accBCaccDA

What is claimed is:

1. A process for the production of an L-amino acid comprising:

culturing recombinant coryneform bacteria under conditions suitable for overexpression of the accDA gene having the nucleic acid sequence comprising SEQ ID NO: 1, and wherein said bacteria produce said L-amino acid selected from the group consisting of L-lysine, L-aspartic acid, L-asparagine, L-homoserine, L-threonine, L-isoleucine, and L-methionine.

2. The process of claim 1, wherein said accDA gene further comprises a nucleotide sequence encoding the polypeptide having an amino acid sequence as set forth in SEQ ID NO: 2.

3. The process of claim 1, wherein said accDA gene comprises polynucleotide sequences which correspond to the sequence of SEQ ID NO: 1 within the region of degeneracy of the genetic code.

4. The process of claim 1, wherein said bacteria is a *Corynebacterium glutamicum*.

5. The process of claim 1, wherein said bacteria further comprises at least one gene other than accDA which is also expressed.

6. The process of claim 1, wherein said bacteria is transformed with a plasmid vector for expressing the accDA gene of *Corynebacterium glutamicum*.

7. The process of claim 6, wherein said vector is pZ1accAD.

8. The process of claim 1, comprising:

culturing coryneform bacteria in which the endogenous accBC gene is overexpressed, under conditions suitable for the production of the accBC gene product.

9. The process of claim 1, wherein an endogenous dapA gene coding for dihydrodipicolinate synthase is simultaneously overexpressed.

10. The process of claim 1, wherein an endogenous DNA fragment conferring S-(2-aminoethyl) cysteine resistance is simultaneously overexpressed.

11. A process for the production of L-amino acids selected from the group consisting of L-lysine, L-aspartic acid, L-asparagine, L-homoserine, L-threonine, L-isoleucine, and L-methionine comprising:

a) culturing recombinant coryneform bacteria in which at least the endogenous accDA gene having the nucleic acid sequence comprising SEQ ID NO: 1 is over expressed, under conditions suitable for the production of the accDA gene product;

b) accumulating the desired L-amino acid in the medium or in the cells of bacteria; and c) isolating the L-amino acid(s); and wherein said bacteria produce said L-amino acid(s).

12. A process for the production of L-amino acids selected from the group consisting of L-lysine, L-aspartic acid, L-asparagine, L-homoserine, L-threonine, L-isoleucine, and L-methionine comprising:

a) culturing recombinant coryneform bacteria in which at least the endogenous accDA gene comprises a nucleic acid sequence encoding an amino acid sequence as set forth in SEQ ID NO: 3 is over expressed conditions suitable for the production of the accDA gene product;

b) accumulating the desired L-amino acid in the medium or in the cells of bacteria; and c) isolating the L-amino acid(s); and wherein said bacteria produce said L-amino acid(s).

13. A process for the production of L-amino acid comprising:

culturing recombinant bacteria under conditions suitable for overexpression of the accDA gene comprising a nucleic acid sequence encoding an amino acid sequence as set forth in SEQ ID NO: 3 and wherein said bacteria produce said L-amino acid selected from the group consisting of L-lysine, L-aspartic acid, L-asparagine, L-homoserine, L-threonine, L-isoleucine, and L-methionine.

14. The process of claim 13, wherein said bacteria is a *Corynebacterium glutamicum*.

15. The process of claim 13, wherein said bacteria further comprises at least one gene other than accDA which is also expressed.

16. The process of claim 13, wherein said bacteria is transformed with a plasmid vector for expressing the accDA gene of *Corynebacterium glutamicum*.

17. The process of claim 16, wherein said vector is pZ1accAD.

18. The process of claim 13, comprising:

culturing coryneform bacteria in which the endogenous accBC gene is overexpressed, under conditions suitable for the production of the accBC gene product.

19. The process of claim 13, wherein an endogenous dapA gene coding for dihydrodipicolinate synthase is simultaneously overexpressed.

20. The process of claim 13, wherein an endogenous DNA fragment conferring S-(2-aminoethyl) cysteine resistance is simultaneously overexpressed.

* * * * *